US008468018B2

(12) United States Patent
Baik

(10) Patent No.: US 8,468,018 B2
(45) Date of Patent: Jun. 18, 2013

(54) APPARATUS AND METHOD FOR CANCELING NOISE OF VOICE SIGNAL IN ELECTRONIC APPARATUS

(75) Inventor: Chang-Hyun Baik, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1023 days.

(21) Appl. No.: 12/493,688

(22) Filed: Jun. 29, 2009

(65) Prior Publication Data

US 2010/0004929 A1 Jan. 7, 2010

(30) Foreign Application Priority Data

Jul. 1, 2008 (KR) ........................ 10-2008-0063467

(51) Int. Cl.

| | |
|---|---|
| ***G10L 21/02*** | (2006.01) |
| ***G10L 15/20*** | (2006.01) |
| ***A61F 11/06*** | (2006.01) |
| ***G10K 11/16*** | (2006.01) |
| ***H03B 29/00*** | (2006.01) |
| ***H04R 3/00*** | (2006.01) |
| ***H04B 15/00*** | (2006.01) |

(52) U.S. Cl.
USPC ....... 704/226; 704/233; 381/71.1; 381/71.11; 381/92; 381/94.1; 381/94.2

(58) Field of Classification Search
USPC ................ 704/226–230, 233; 381/94.1–94.3, 381/94.7
See application file for complete search history.

(56) References Cited

U.S. PATENT DOCUMENTS

| | | | | |
|---|---|---|---|---|
| 7,636,448 | B2 * | 12/2009 | Metcalf | 381/300 |
| 7,657,038 | B2 * | 2/2010 | Doclo et al. | 381/94.1 |
| 7,944,775 | B2 * | 5/2011 | Sugiyama | 367/135 |
| 7,957,542 | B2 * | 6/2011 | Sarrukh et al. | 381/92 |
| 8,005,238 | B2 * | 8/2011 | Tashev et al. | 381/94.2 |
| 8,014,230 | B2 * | 9/2011 | Sugiyama | 367/135 |
| 8,106,827 | B2 * | 1/2012 | Sugiyama | 342/383 |
| 8,174,935 | B2 * | 5/2012 | Sugiyama | 367/135 |
| 8,194,852 | B2 * | 6/2012 | Buck et al. | 379/406.14 |
| 8,194,872 | B2 * | 6/2012 | Buck et al. | 381/71.11 |
| 2005/0147258 | A1 * | 7/2005 | Myllyla et al. | 381/71.11 |
| 2006/0222184 | A1 * | 10/2006 | Buck et al. | 381/71.1 |
| 2007/0055505 | A1 * | 3/2007 | Doclo et al. | 704/226 |
| 2007/0076898 | A1 * | 4/2007 | Sarroukh et al. | 381/92 |
| 2007/0273585 | A1 * | 11/2007 | Sarroukh et al. | 342/379 |
| 2008/0144848 | A1 * | 6/2008 | Buck et al. | 381/66 |
| 2008/0232607 | A1 * | 9/2008 | Tashev et al. | 381/71.11 |
| 2009/0034752 | A1 * | 2/2009 | Zhang et al. | 381/92 |

(Continued)

OTHER PUBLICATIONS

Hoshuyama, O.; Sugiyama, A.; Hirano, A.; , "A robust adaptive beamformer for microphone arrays with a blocking matrix using constrained adaptive filters," Signal Processing, IEEE Transactions on , vol. 47, No. 10, pp. 2677-2684, Oct. 1999.*

(Continued)

*Primary Examiner* — Paras D Shah
*Assistant Examiner* — Matthew Baker
(74) *Attorney, Agent, or Firm* — Jefferson IP Law, LLP

(57) ABSTRACT

An apparatus and a method for canceling noise in a voice signal in an electronic apparatus are provided. The apparatus includes a Generalized Sidelobe Canceller (GSC) and a decision unit. The GSC cancels noise components from signals with different phases input via a plurality of microphones. The decision unit estimates a Signal-to-Noise Ratio (SNR) of an input signal to determine a step-size of a filter included in the GSC.

7 Claims, 4 Drawing Sheets

U.S. PATENT DOCUMENTS

| | | | | |
|---|---|---|---|---|
| 2009/0073040 | A1* | 3/2009 | Sugiyama | 342/378 |
| 2009/0086578 | A1* | 4/2009 | Sugiyama | 367/138 |
| 2009/0121934 | A1* | 5/2009 | Sugiyama | 342/372 |
| 2010/0004929 | A1* | 1/2010 | Baik | 704/233 |
| 2010/0171662 | A1* | 7/2010 | Sugiyama | 342/378 |
| 2011/0274291 | A1* | 11/2011 | Tashev et al. | 381/94.1 |

OTHER PUBLICATIONS

Herbordt, W.; Kellermann, W.; , "Efficient frequency-domain realization of robust generalized, sidelobe cancellers," Multimedia Signal Processing, 2001 IEEE Fourth Workshop on , vol., no., pp. 377-382, 2001.*

Herbordt, W.; Kellermann, W; Frequency-domain integration of acoustic echo cancellation and a generalized sidelobe canceller with improved robustness. Eur. Trans. Telecomm., vol. 12, iss. 2. 2002.*

Min-Seok Choi; Chang-Hyun Baik; Young-Cheol Park; Hong-Goo Kang; , "A Soft-Decision Adaptation Mode Controller for an Efficient Frequency-Domain Generalized Sidelobe Canceller," Acoustics, Speech and Signal Processing, 2007. ICASSP 2007. IEEE International Conference on , vol. 4, no., pp. IV-893-IV-896, Apr. 15-20, 2007.*

Wei Liu; Weiss, S.; Hanzo, L.; , "Subband adaptive generalized sidelobe canceller for broadband beamforming," Statistical Signal Processing, 2001. Proceedings of the 11th IEEE Signal Processing Workshop on , vol., no., pp. 591-594, 2001.*

Markus Buck, Tim Haulick, Hans-Jorg Pfleiderer. Self-calibrating micrpohone arrays for speech signal acquisition: a systematic approach. Signal Processing. Received Jan. 2, 2005. Revised Feb. 24, 2005. Accepted Jun. 9, 2005. Available online Oct. 19, 2005.*

* cited by examiner

APPARATUS AND METHOD FOR CANCELING NOISE OF VOICE SIGNAL IN ELECTRONIC APPARATUS

PRIORITY

This application claims the benefit under 35 U.S.C. §119 (a) of a Korean patent application filed in the Korean Intellectual Property Office on Jul. 1, 2008 and assigned Serial No. 10-2008-0063467, the entire disclosure of which is hereby incorporated by reference.

BACKGROUND OF THE INVENTION

1. Field of the Invention

The present invention relates to an apparatus and a method for canceling noise in a voice signal in an electronic apparatus. More particularly, the present invention relates to an apparatus and a method for canceling noise in a voice signal by adaptively changing a step-size of a filter in a Generalized Sidelobe Canceller (GSC)-based electronic apparatus.

2. Description of the Related Art

As various electronic apparatuses are provided due to recent developments in electronic technology, interest in a Human Machine Interface (HMI) has been increased. That is, research has been variously performed on methods for allowing an electronic apparatus to be used easily by allowing a user to communicate with the electronic apparatus. For example, research has been performed on a method for recognizing and processing a user's voice in the electronic apparatus.

Most of currently provided voice recognition modules represent high performance approaching 100% under a noise-free environment. However, various noises exist in a real environment and the performance of the voice recognition module deteriorates. Therefore, a conventional speech enhancement algorithm has been used as a pre-process of voice recognition.

The speech enhancement algorithm for the pre-process of the voice recognition may be classified into a single-channel algorithm which uses one microphone and a multi-channel algorithm which uses a plurality of microphones. In the multi-channel algorithm, a beamforming algorithm is provided. The beamforming algorithm enhances a voice by determining a position of a user, i.e., a speaker, using an angle of a voice signal input via a microphone, maintaining the gain of a signal input from a direction determined as the position of the speaker, and reducing the gains of signals input from the other directions. The above-described speech enhancement algorithm which uses the beamforming includes a fixed beamformer, a Linearly Constrained Minimum Variance (LCMV) beamformer, and a Generalize Sidelobe Canceller (GSC). The conventional electronic apparatus, as described below, uses the GSC.

FIG. 1 illustrates a structure of a conventional GSC. Referring to FIG. 1, when signals $x_0(k)$ to $x_{N-1}(k)$ having different phases are input via N microphones 100, 102 and 104, the GSC obtains a noise-reduced signal by compensating for only a phase of a user's voice signal using a Fixed Beam Former (FBF) 110, and then adding signals 150 of respective channels input via the N microphones 100, 102 and 104. Since the FBF 110 compensates for only a phase of an object signal, i.e., the voice signal using a plurality of microphones, the noise signal is reduced to a size of 1/N. Also, the GSC extracts only noise components by subtracting signals input for respective channels via a Blocking Matrix (BM) 120 in order to cancel noise which has not been cancelled by the FBF, and obtains a noise-cancelled final signal by combining the extracted noise components using a Multiple Input Canceller (MIC) 130 and subtracting the combined noise components from an output of the FBF 110. At this point, conventional adaptive filters may be used as the BM 120 and the MIC 130. The adaptive filters perform adaptive filtering in a voice section and a mute section, respectively, according to a control command of an Adaptive Mode Controller (AMC) 140 for dividing a voice signal into the voice section and the mute section. Here, the voice section denotes a section where a user's voice exists, and the mute section denotes a section where only noise exists and the voice does not exists.

In the above-described GSC, the BM 120 and the MIC 130 control coefficients of the filters using fixed step-sizes μ. However, since the noise has a non-stationary characteristic, when the fixed step-sizes are used, speech enhancement is difficult to perform properly.

Therefore, a need exists for an apparatus and method for canceling noise in an electronic apparatus while performing speech enhancement.

SUMMARY OF THE INVENTION

An aspect of the present invention is to address at least the above mentioned problems and/or disadvantages and to provide at least the advantages described below. Accordingly, an aspect of the present invention is to provide an apparatus and a method for canceling noise in a voice signal in an electronic apparatus.

Another aspect of the present invention is to provide an apparatus and a method for canceling noise based on a non-stationary noise characteristic in an electronic apparatus.

Still another aspect of the present invention is to provide an apparatus and a method for canceling noise by adaptively changing a step-size of a noise cancel filter according to a Signal-to-Noise Ratio (SNR) in a voice signal in an electronic apparatus.

In accordance with an aspect of the present invention, an apparatus for canceling noise in a voice signal in an electronic apparatus is provided. The apparatus includes a Generalized Sidelobe Canceller (GSC) for canceling noise components from signals with different phases input via a plurality of microphones, and a decision unit for estimating a Signal-to-Noise Ratio (SNR) of an input signal to determine a step-size of filters included in the GSC.

In accordance with another aspect of the present invention, a method for canceling noise in a voice signal in an electronic apparatus is provided. The method includes estimating a Signal-to-Noise Ratio (SNR) of a signal input via one of a plurality of microphones, determining a step-size of each filter included in a Generalized Sidelobe Canceller (GSC) according to the SNR, and canceling noise components from signals input via the plurality of microphones by performing filtering according to the determined step-size.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWINGS

The above and other aspects, features and advantages of certain exemplary embodiments of the present invention will be more apparent from the following description taken in conjunction with the accompanying drawings, in which.

Throughout the drawings, it should be noted that like reference numbers are used to depict the same or similar elements, features and structures.

DETAILED DESCRIPTION OF EXEMPLARY EMBODIMENTS

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Exemplary embodiments of the present invention provide an apparatus and a method for canceling noise in a voice signal by adaptively changing a step-size of a filter according to a Signal-to-Noise Ratio (SNR) in an electronic apparatus which supports a Generalized Sidelobe Canceller (GSC) system.

Figure 1:
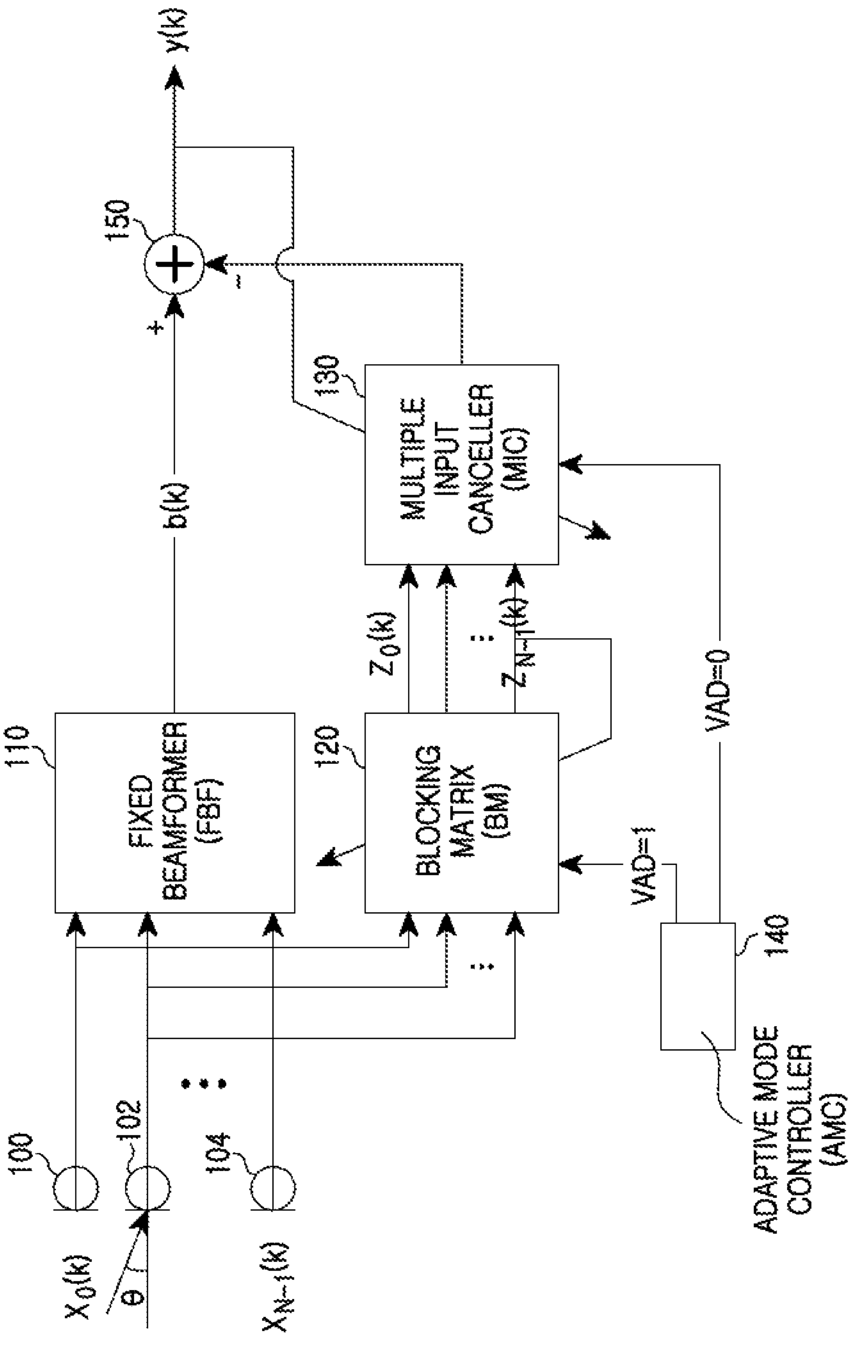
FIG. 1 (CONVENTIONAL ART)
FIG. 1 is a view illustrating a structure of a conventional Generalized Sidelobe Canceller (GSC)
Figure 2:
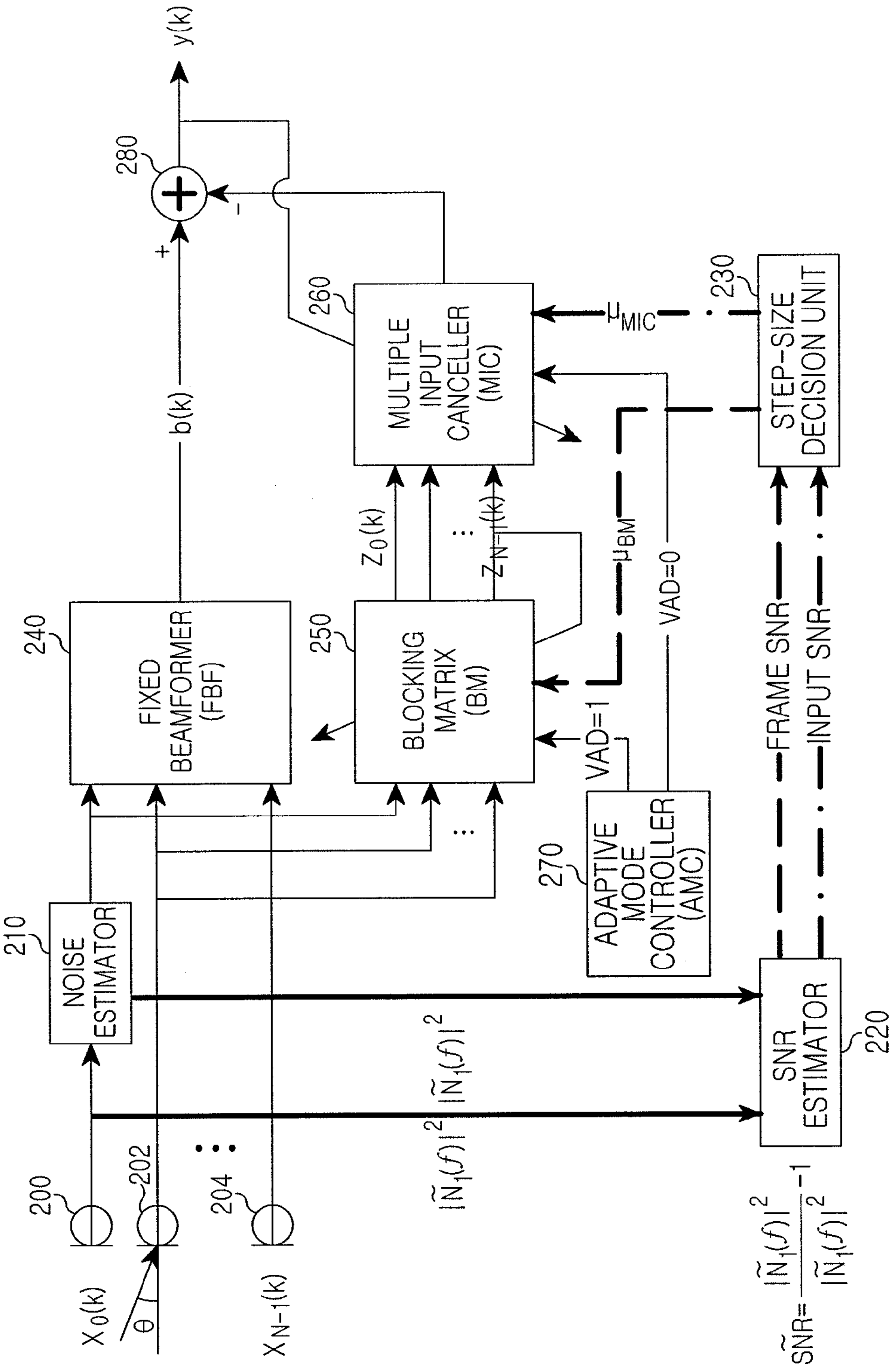
FIG. 2 is a view illustrating a structure for canceling noise in a voice signal in an electronic apparatus according to an exemplary embodiment of the present invention.

FIG. 2 is a view illustrating a structure for canceling noise in a voice signal in an electronic apparatus according to an exemplary embodiment of the present invention.

Referring to FIG. 2, similar to the conventional GSC system, the electronic apparatus includes N microphones 200, 202 and 204, a Fixed Beam Former (FBF) 240, a Blocking Matrix (BM) 250, a Multiple Input Canceller (MIC) 260, an Adaptive Mode Controller (AMC) 270 and an adder 280. The electronic apparatus further includes a noise estimator 210, an SNR estimator 220 and a step-size decision unit 230.

The noise estimator 210 estimates noise power in a frequency domain with respect to one of signals input via the N microphones 200, 202 and 204. For example, the noise estimator 210 uses a noise estimation technique which is primarily used for a single-channel speech enhancement algorithm.

The SNR estimator 220 measures a signal power value in the frequency domain with respect to one of the signals input via the N microphones 200, 202 and 204, and estimates an SNR as in Equation (1) using the noise power estimated by the noise estimator 210 and the signal power value.

$$\tilde{SNR} = \frac{|X_1(f)|^2}{|\tilde{N}_1(f)|^2} - 1 \quad (1)$$

In Equation (1), $\tilde{SNR}$ is an estimated signal-to-noise ratio, $|X_1(f)|^2$ is the power of a signal input via a first channel, and $|\tilde{N}_1(f)|^2$ is the noise power of a signal input via the first channel.

At this point, the SNR estimator 220 estimates the SNR on a frame basis for the BM 250 and estimates the SNR of a predefined section greater than a frame for the MIC 260. Here, a reference of an SNR for determining a step-size of the BM 250 is different from the reference of an SNR for determining a step-size of the MIC 260 because the BM 250 performs adaptive filtering in a voice section (VAD=1) and the MIC 260 performs adaptive filtering in a mute section (VAD=0). That is, both voice and noise exist in the voice section, the SNR estimator 220 may obtain an SNR on a frame basis. On the other hand, since a voice signal does not exist in the mute section and noise exists in the mute section, the SNR estimator 220 estimates an SNR for the predefined section greater than the frame for the MIC 260.

Figure 3A:
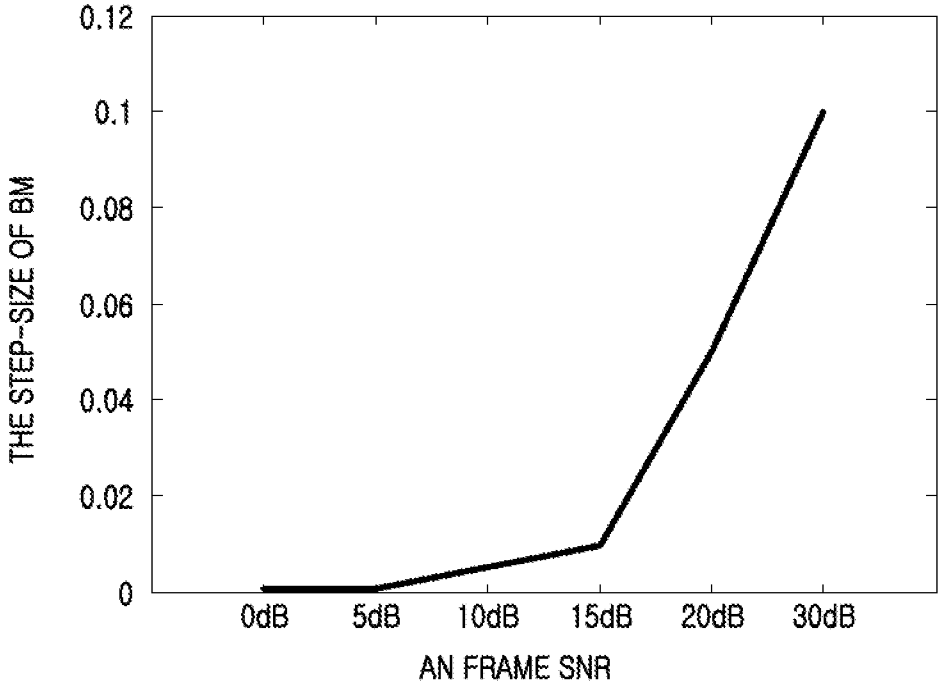
FIGS. 3A and 3B are graphs illustrating a step-size magnitude according to a Signal-to-Noise Ratio (SNR) in an electronic apparatus according to an exemplary embodiment of the present invention.
Figure 3B:
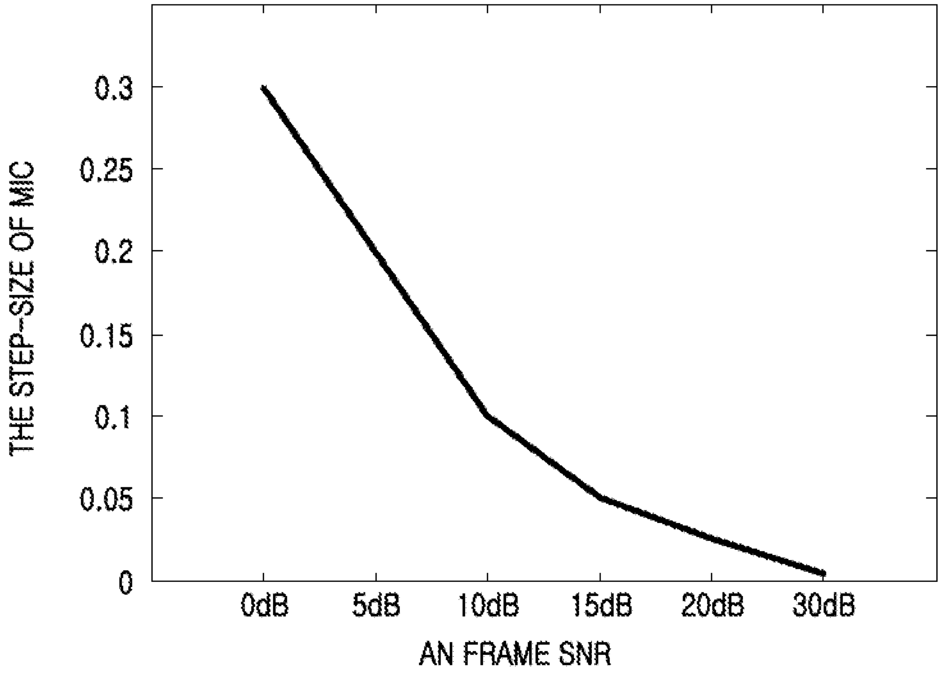

The step-size decision unit 230 determines step-sizes of the BM 250 and the MIC 260 according to the SNR for each frame and the SNR of the predefined section provided from the SNR estimator 220, respectively. Accordingly, the step-size decision unit 230 stores in advance a mapping table representing a step-size according to the SNR for each frame and a mapping table representing a step-size according to the SNR of the predefined section. The two mapping tables may be generated based on graphs illustrated in FIGS. 3A and 3B for each SNR. FIGS. 3A and 3B illustrate a step-size magnitude according to an SNR in an electronic apparatus according to an exemplary embodiment of the present invention.

The FBF 240 receives signals $x_0(k)$ to $x_{N-1}(k)$ having different phases via the N microphones 200, 202 and 204, compensates for the phase of a user's voice signal, adds signals input for respective channels via the N microphones 200, 202 and 204, and outputs a noise-reduced signal b(k). Since the FBF 240 compensates for the phase of a voice signal, which is an object signal, using the N microphones, the noise signal reduces to 1/N in size.

The BM 250 cancels voice signals of adjacent channels by performing inter-adjacent channel subtraction on signals $x_0(k)$ to $x_{N-1}(k)$ input for respective channels via the N microphones 200, 202 and 204 in a voice section (VOD=1) where a voice signal exists under control of the AMC 270. In other words, among the signals input for respective channels via the N microphones 200, 202 and 204, the BM 250 subtracts a signal of a second channel from a signal of a first channel, subtracts a signal of a third channel from a signal of a second channel, and subtracts a signal of a Nth channel from a signal of a (N−1)th channel, thereby obtaining only noise components $z_0(k)$ to $z_{N-1}(k)$ of respective channel signals. Here, $z_0(k)$ denotes $x_0(k)$-$x_1(k)$, $z_1(k)$ denotes $x_1(k)$-$x_2(k)$, and $z_{N-1}(k)$ denotes $x_{N-1}(k)$-$x_N(k)$. More particularly, the BM 250 performs adaptive filtering according to a step-size $\mu_{BM}$ provided from the step-size decision unit 230 in a section where a voice signal exists according to an exemplary embodiment of the present invention.

The MIC 260 combines and outputs the noise components $z_0(k)$ to $Z_{N-1}(k)$ extracted from the BM 250 in a mute section (VAD=0) where a voice signal does not exist under control of the AMC 270. More particularly, the MIC 260 performs adaptive filtering according to a step-size pMIC provided from the step-size decision unit 230 in a mute section where a voice signal does not exist according to an exemplary embodiment of the present invention.

The AMC 270 determines voice sections and mute sections of signals $x_0(k)$ to $x_{N-1}(k)$ input for respective channels via the N microphones 200, 202 and 204, outputs a signal (VAD=1) informing a voice section to the BM 250 during the voice section, and outputs a signal (VAD=0) informing a mute section to the MIC 260 during the mute section.

The adder 280 cancels a noise signal from an output b(k) of the FBF 240 by summing the output b(k) of the FBF 240 and an output of the MIC 260.

Figure 4:
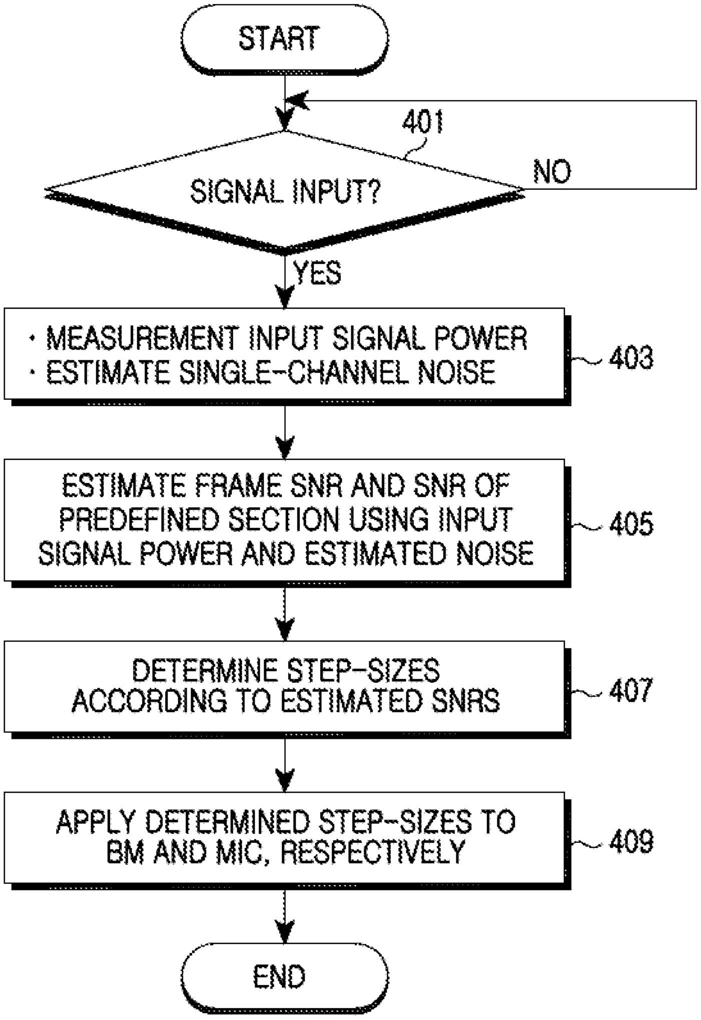
FIG. 4 is a flowchart for controlling a step-size magnitude in an electronic apparatus according to an exemplary embodiment of the present invention.

FIG. 4 is a flowchart for controlling a step-size magnitude in an electronic apparatus according to an exemplary embodiment of the present invention.

Referring to FIG. 4, in step 401, the electronic apparatus determines whether a user's voice signal is input via N microphones. In step 403, the electronic apparatus measures the power of a voice signal input via one microphone among voice signals input via the N microphones and estimates noise power. At this point, the estimation of the power of the voice signal and the noise power are performed in a frequency domain.

In step 405, the electronic apparatus estimates an SNR on a frame basis, and an SNR of a predefined section greater than the frame using the power of the input signal and the estimated noise power. The SNR may be determined as in Equation (1).

In step 407, the electronic apparatus determines a step-size according to the estimated SNR on the frame basis and a step-size according to the estimated SNR of the predefined section with reference to a mapping table stored in advance.

In step 409, the electronic apparatus applies the determined step-sizes to the BM and the MIC, respectively, to perform filtering, and ends the operation according to an exemplary embodiment of the present invention.

Exemplary embodiments of the present invention improve a voice recognition rate under various noise environments and SNR environments by adaptively changing the step-sizes of filters depending on SNRs of a voice signal to cancel a noise in an electronic apparatus which supports a GSC.

While the invention has been shown and described with reference to certain exemplary embodiments thereof, it will be understood by those skilled in the art that various changes in form and details may be made therein without departing from the spirit and scope of the invention as defined by the appended claims and their equivalents.

What is claimed is:

1. An apparatus for canceling noise in a voice signal in an electronic apparatus, the apparatus comprising:

a Generalized Sidelobe Canceller (GSC) for canceling noise components from signals with different phases input via a plurality of microphones; and a decision unit for estimating a Signal-to-Noise Ratio (SNR) of an input signal to be inputted to the GSC, and for determining a step-size of filters included in the GSC based on the SNR, wherein the decision unit comprises:

a noise estimator for estimating noise power of a signal input via one of the plurality of microphones;

an SNR estimator for estimating the SNR using power of a signal input via at least one of the microphones and the noise power; and a step-size decision unit for determining the step-size of the filters according to the estimated SNR using a mapping table set in advance, wherein the SNR estimator estimates the SNR on a frame basis, and an SNR of a predefined section greater than a frame, wherein the step-size decision unit determines the step-size according to the SNR on the frame basis and the step-size according to the SNR of the predefined section using the mapping table, and wherein the step-size is determined according to the SNR on the frame basis is applied to a filter of a Blocking Matrix (BM) included in the GSC, and the step-size determined according to the SNR of the predefined section is applied to a filter of a Multiple Input Canceller (MIC) included in the GSC.

2. The apparatus of claim 1, wherein the GSC comprises:

a Blocking Matrix (BM) for canceling a voice signal for each adjacent channel in a voice section of the input signal using a filter to obtain the noise components; and a Multiple Input Canceller (MIC) for combining the obtained noise components in a mute section of the input signal using a filter.

3. The apparatus of claim 2, wherein the decision unit determines step-sizes of the filters used for the BM and the MIC, respectively.

4. A method for canceling noise in a voice signal in an electronic apparatus, the method comprising:

estimating a Signal-to-Noise Ratio (SNR) of a signal input via one of a plurality of microphones;

determining a step-size of each filter included in a Generalized Sidelobe Canceller (GSC) according to the SNR; and canceling noise components from signals input via the plurality of microphones by performing filtering according to the determined step-size, wherein the estimating of the SNR comprises:

measuring power of a signal input via one of the microphones;

estimating noise power of a signal input via one of the microphones;

estimating the SNR using the power of the signal and the noise power of the signal, and estimating the SNR on a frame basis with respect to the signal input via one of the microphones, and the SNR of a predefined section greater than a frame, wherein the determining of the step-size of each filter comprises determining a step-size of a filter according to the SNR on the frame basis, and a step-size of a filter according to the SNR of the predefined section using a mapping table set in advance, and wherein the step-size of the filter determined according to the SNR on the frame basis is applied to a filter of a Blocking Matrix (BM) included in the GSC, and the step-size of the filter determined according to the SNR of the predefined section is applied to a filter of a Multiple Input Canceller (MIC) included in the GSC.

5. An apparatus for canceling voice in a voice signal in an electronic apparatus supporting a Generalized Sidelobe Canceller (GSC) system, the apparatus comprising:

a noise estimator for estimating noise power of a signal input via one of a plurality of microphones;

a Signal-to-Noise Ratio (SNR) estimator for estimating an SNR using power of a signal input via at least one of the plurality of microphones and the noise power;

and a step-size decision unit for determining the step-size of a filter of a Blocking Matrix (BM) and a filter of a Multiple Input Canceller (MIC) according to the estimated SNR using a mapping table set in advance, wherein the SNR estimator estimates the SNR on a frame basis and an SNR of a predefined section greater than a frame, and wherein the step-size decision unit determines the step size of the filter of the BM according to the SNR on the frame basis and determines the step-size of the filter of the MIC according to the SNR of the predefined section using the mapping table.

6. The apparatus of claim 5, wherein the BM cancels a voice signal for each adjacent channel in a voice section of the input signal using the filter to obtain the noise components.

7. The apparatus of claim 5, wherein the MIC combines the obtained noise components in a mute section of the input signal using the filter.

* * * * *